(12) United States Patent
Laban et al.

(10) Patent No.: US 7,030,251 B2
(45) Date of Patent: Apr. 18, 2006

(54) MODIFICATIONS OF THE TROMETAMOL SALT OF R-THIOCTIC ACID AS WELL AS A PROCESS FOR THEIR PRODUCTION

(75) Inventors: Gunter Laban, Dresden-Langebrück (DE); Wolfgang Sauer, Dresden (DE); Annegret Jannasch, Moritzburg (DE)

(73) Assignee: Viatris GmbH & Co KG, Frankfurt am Main (DE)

( * ) Notice: Subject to any disclaimer, the term of this patent is extended or adjusted under 35 U.S.C. 154(b) by 0 days.

(21) Appl. No.: 10/870,157

(22) Filed: Jun. 18, 2004

(65) Prior Publication Data

US 2004/0225007 A1 Nov. 11, 2004

Related U.S. Application Data

(62) Division of application No. 10/207,201, filed on Jul. 30, 2002, now Pat. No. 6,844,449.

(30) Foreign Application Priority Data

Jul. 31, 2001 (DE) ................................ 101 37 381

(51) Int. Cl.
*C07D 339/02* (2006.01)
*A61K 31/385* (2006.01)
(52) U.S. Cl. ........................ 549/39; 514/440
(58) Field of Classification Search .................. 549/39; 514/440
See application file for complete search history.

(56) References Cited

U.S. PATENT DOCUMENTS

| 5,948,810 A | 9/1999 | Wessel et al. |
| 6,369,098 B1 * | 4/2002 | Pershadsingh et al. ...... 514/440 |
| 6,387,945 B1 * | 5/2002 | Packer et al. ............... 514/440 |
| 6,441,024 B1 | 8/2002 | Klatt et al. |
| 6,605,637 B1 * | 8/2003 | Harnett et al. .............. 514/440 |
| 6,670,484 B1 * | 12/2003 | Villani et al. ................. 549/39 |
| 6,844,450 B1 * | 1/2005 | Salvi et al. ................... 549/39 |

FOREIGN PATENT DOCUMENTS

| DE | 40 37 440 A1 | 5/1992 |
| DE | 41 37 773 A1 | 5/1993 |
| DE | 43 43 592 A1 | 6/1995 |
| DE | 43 43 593 A1 | 6/1995 |
| DE | 195 33 881 A1 | 3/1997 |
| DE | 195 33 882 A1 | 3/1997 |
| DE | 198 18 563 A1 | 10/1999 |
| DE | 197 09 069 A1 | 4/2000 |
| EP | 0 427 247 A2 | 5/1991 |
| EP | 0 702 953 A2 | 8/1995 |

* cited by examiner

*Primary Examiner*—Deborah C. Lambkin
(74) *Attorney, Agent, or Firm*—Buchanan Ingersoll PC

(57) ABSTRACT

The invention relates to new modifications of the trometamol salt of R-thioctic acid of the formula I,

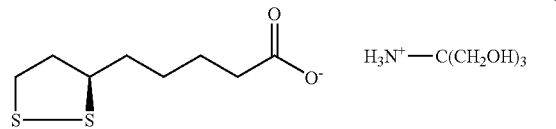

processes for their production, pharmaceutical preparations containing these modifications, and their medical application.

2 Claims, 6 Drawing Sheets

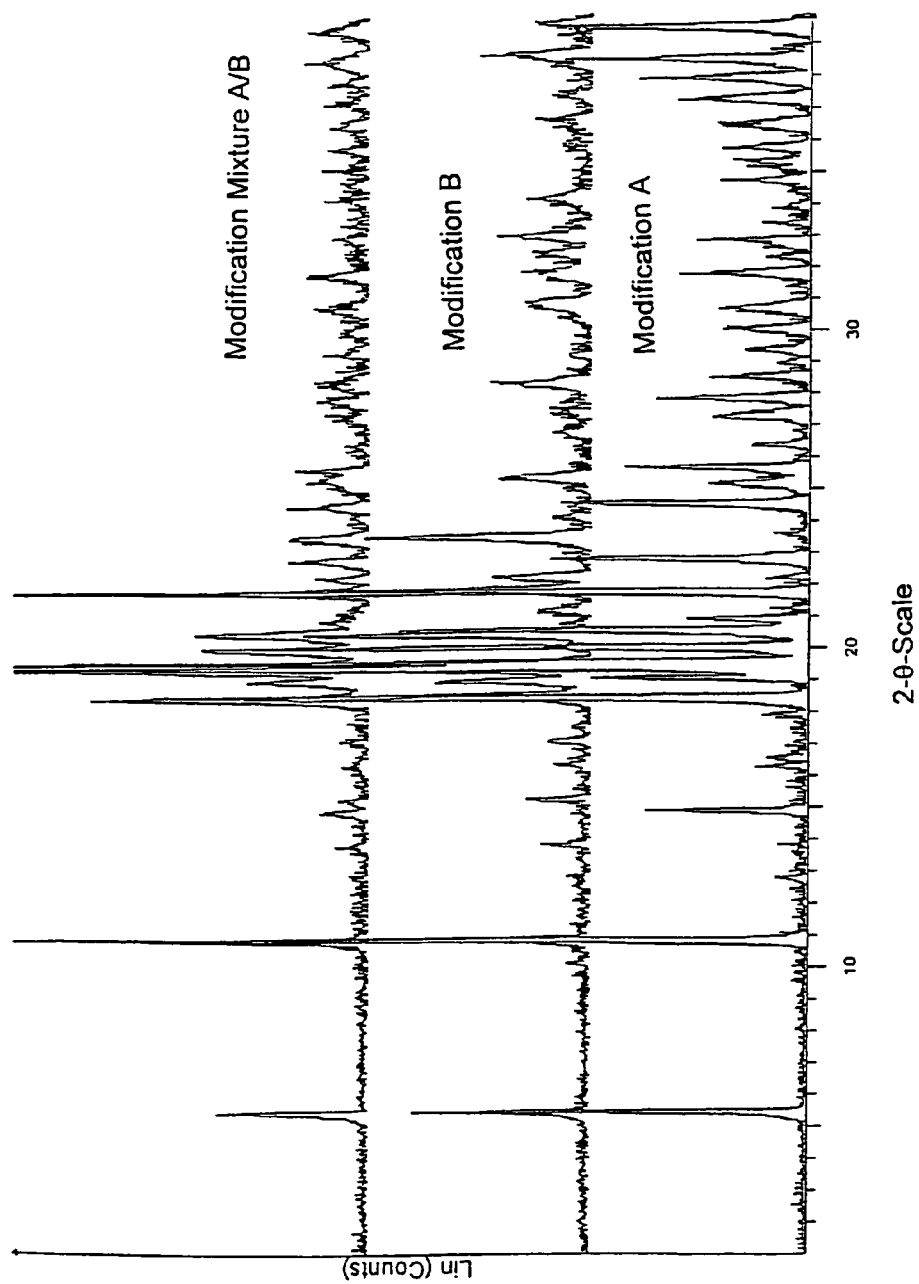
Fig. 1: Trometamol Salt of R-thioctic Acid

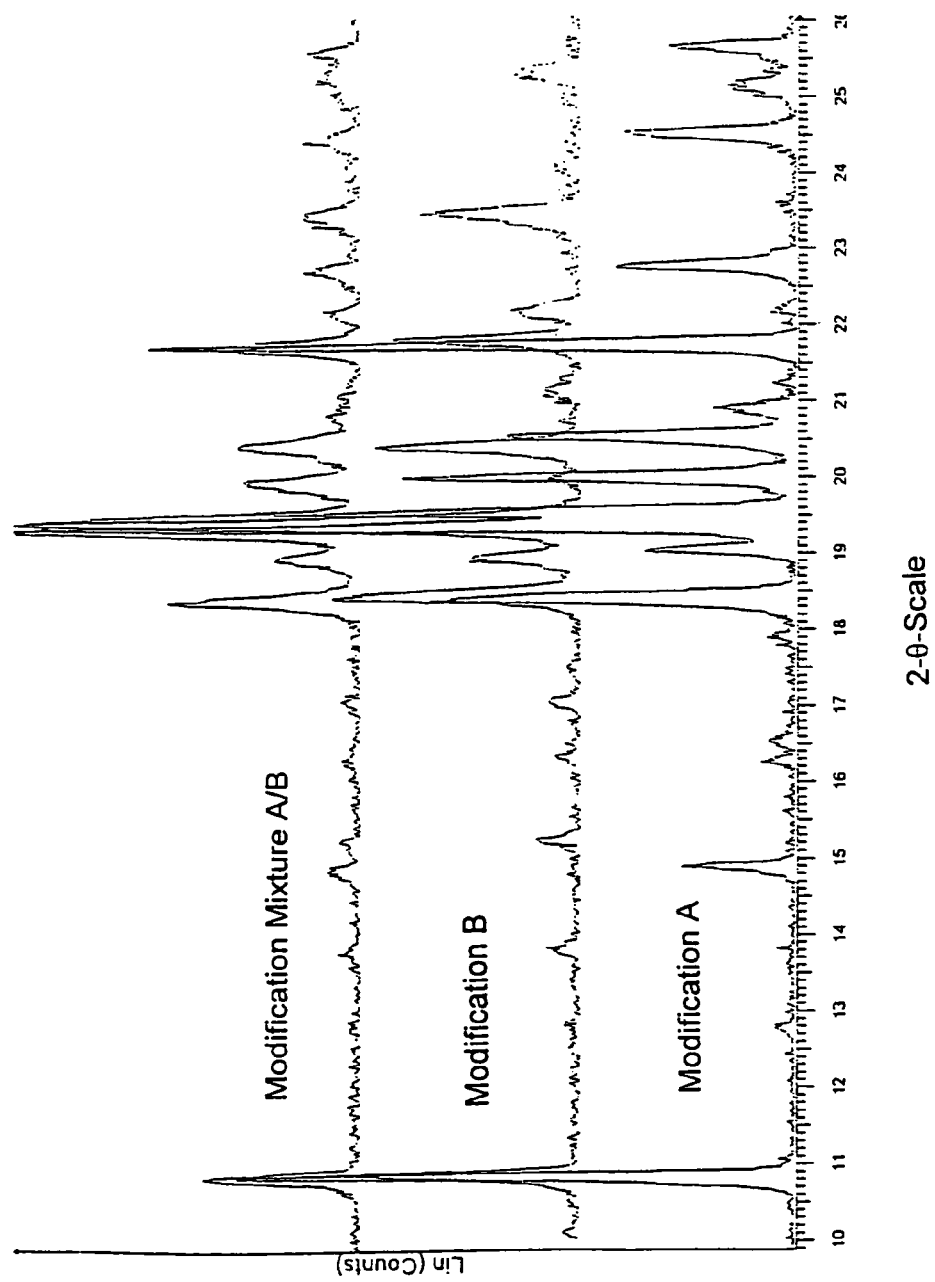
Fig. 2: Trometamol Salt of R-thioctic Acid: Range 10° to 26°C 2θ

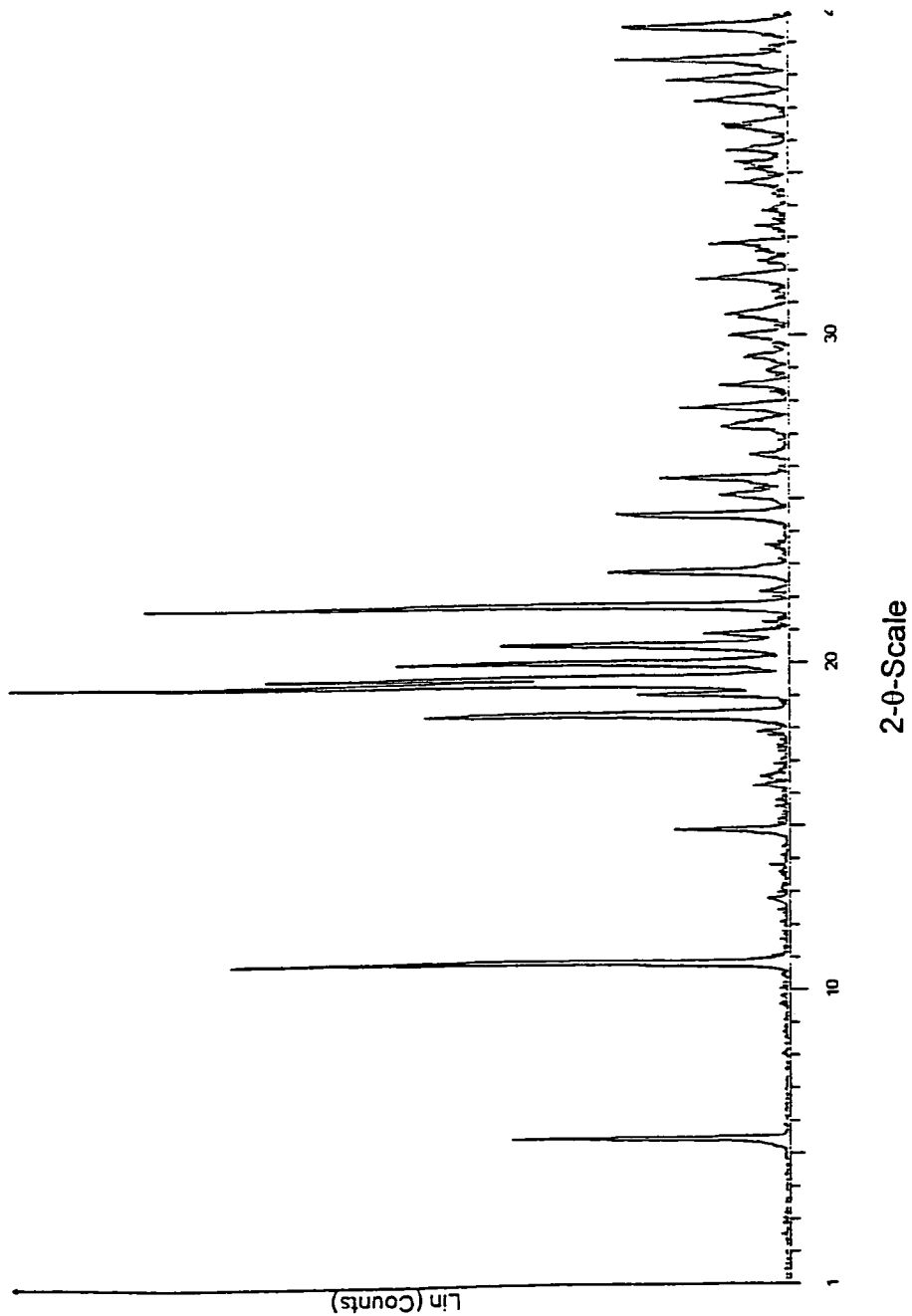
Fig. 3: Trometamol Salt of R-thioctic Acid, Modification A

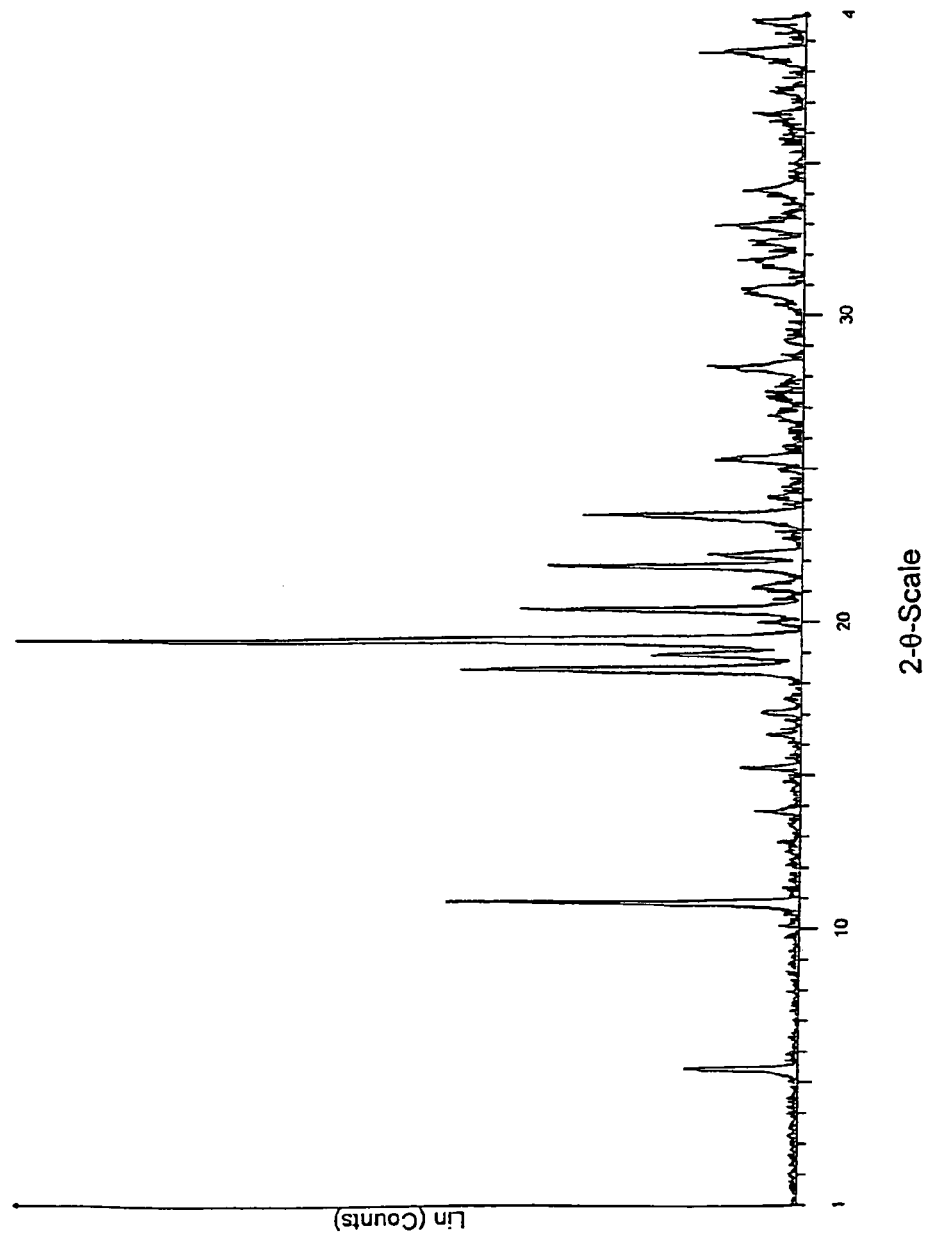
Fig. 4: Trometamol Salt of R-thioctic Acid, Modification B

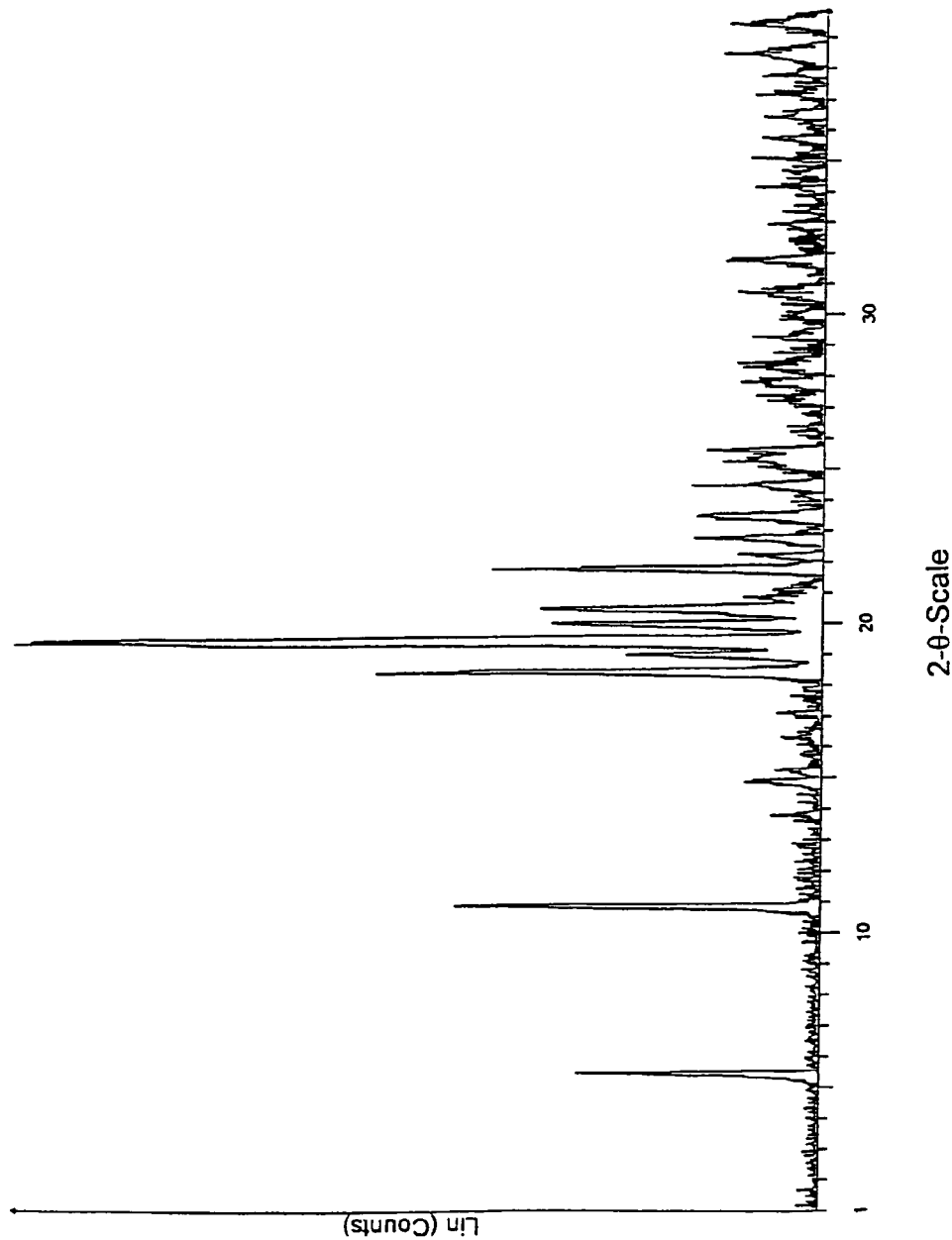
Fig. 5: Trometamol Salt of R-thioctic Acid, Modification Mixture A/B

Fig. 6: Powder Data of the Modifications of the Trometamol Salt of R-thioctic Acid

| Modification A | | | Modification B | | | Modification Mixture A/B | | |
|---|---|---|---|---|---|---|---|---|
| 2θ (°) | d-value (Å) | Intensity (%) | 2θ (°) | d-value (Å) | Intensity (%) | 2θ (°) | d-value (Å) | Intensity (%) |
| 5.42 | 16.31 | 35 | 5.39 | 16.40 | 13 | 5.39 | 16.39 | 33 |
|  |  |  | 10.10 | 8.75 | 3 |  |  |  |
| 10.80 | 8.19 | 71 | 10.83 | 8.16 | 41 | 10.81 | 8.18 | 50 |
| 12.74 | 6.94 | 3 |  |  |  | 12.78 | 6.92 | 3 |
|  |  |  | 13.80 | 6.41 | 6 | 13.78 | 6.42 | 7 |
| 14.87 | 5.96 | 15 |  |  |  | 14.84 | 5.97 | 11 |
|  |  |  | 15.22 | 5.82 | 8 | 15.20 | 5.82 | 6 |
| 16.26 | 5.45 | 5 | 16.31 | 5.43 | 4 | 16.32 | 5.43 | 3 |
| 16.53 | 5.36 | 4 |  |  |  |  |  |  |
|  |  |  | 17.05 | 5.20 | 5 | 17.06 | 5.20 | 6 |
|  |  |  | 17.50 | 5.06 | 2 |  |  |  |
| 17.90 | 4.95 | 4 |  |  |  |  |  |  |
| 18.41 | 4.82 | 46 | 18.45 | 4.81 | 45 | 18.40 | 4.82 | 61 |
| 19.04 | 4.66 | 20 | 18.94 | 4.68 | 19 | 18.96 | 4.68 | 27 |
| 19.35 | 4.58 | 100 | 19.41 | 4.57 | 100 | 19.32 | 4.59 | 100 |
| 19.54 | 4.54 | 67 |  |  |  | 19.43 | 4.57 | 97 |
| 19.99 | 4.44 | 50 | 19.96 | 4.45 | 6 | 19.95 | 4.45 | 36 |
| 20.54 | 4.32 | 37 | 20.41 | 4.35 | 37 | 20.44 | 4.34 | 39 |
| 20.88 | 4.25 | 11 |  |  |  | 20.83 | 4.26 | 10 |
| 21.24 | 4.18 | 3 | 21.13 | 4.20 | 6 |  |  |  |
| 21.74 | 4.09 | 83 | 21.82 | 4.07 | 33 | 21.74 | 4.09 | 45 |
| 22.22 | 4.00 | 3 | 22.19 | 4.00 | 12 | 22.17 | 4.01 | 9 |
| 22.78 | 3.90 | 23 |  |  |  | 22.74 | 3.91 | 18 |
| 23.57 | 3.77 | 2 | 23.48 | 3.79 | 29 | 23.47 | 3.79 | 17 |
| 24.53 | 3.63 | 22 | 24.09 | 3.69 | 5 | 24.47 | 3.64 | 18 |
| 25.15 | 3.54 | 9 | 25.00 | 3.56 | 3 |  |  |  |
|  |  |  | 25.33 | 3.51 | 11 | 25.29 | 3.52 | 14 |
|  |  |  |  |  |  | 25.61 | 3.48 | 16 |
| 25.66 | 3.47 | 17 |  |  |  |  |  |  |
| 26.37 | 3.38 | 5 | 26.75 | 3.33 | 5 | 26.36 | 3.38 | 4 |
| 27.26 | 3.27 | 9 | 27.34 | 3.26 | 4 | 27.27 | 3.27 | 5 |
| 27.85 | 3.20 | 14 |  |  |  | 27.84 | 3.20 | 11 |
| 28.53 | 3.13 | 8 | 28.31 | 3.15 | 11 | 28.28 | 3.15 | 11 |
| 28.97 | 3.08 | 3 | 29.18 | 3.06 | 2 |  |  |  |
| 29.38 | 3.04 | 6 |  |  |  | 29.28 | 3.05 | 10 |
| 30.05 | 2.97 | 8 |  |  |  | 29.95 | 2.98 | 6 |
|  |  |  | 30.36 | 2.94 | 3 |  |  |  |
| 30.70 | 2.91 | 8 | 30.86 | 2.90 | 8 | 30.70 | 2.91 | 11 |
| 31.80 | 2.81 | 12 | 31.85 | 2.81 | 9 | 31.80 | 2.81 | 14 |
| 32.32 | 2.77 | 4 |  |  |  | 32.42 | 2.76 | 5 |
|  |  |  | 32.45 | 2.76 | 6 | 32.48 | 2.75 | 5 |
| 32.88 | 2.72 | 9 | 32.97 | 2.71 | 12 | 32.95 | 2.72 | 8 |
| 33.39 | 2.68 | 4 | 33.36 | 2.68 | 3 | 33.37 | 2.68 | 6 |
| 33.92 | 2.64 | 2 |  |  |  | 34.12 | 2.63 | 5 |
| 34.76 | 2.58 | 8 | 34.20 | 2.62 | 6 | 34.64 | 2.59 | 5 |
|  |  |  |  |  |  | 35.08 | 2.56 | 6 |
| 35.37 | 2.54 | 7 |  |  |  |  |  |  |
| 35.78 | 2.51 | 6 | 35.78 | 2.51 | 3 | 35.75 | 2.51 | 9 |
| 36.51 | 2.46 | 8 | 36.67 | 2.45 | 5 | 36.62 | 2.45 | 6 |
| 37.29 | 2.41 | 10 | 37.42 | 2.40 | 5 | 37.21 | 2.41 | 7 |
| 37.94 | 2.37 | 15 |  |  |  | 37.86 | 2.37 | 8 |
| 38.54 | 2.33 | 22 | 38.69 | 2.33 | 14 | 38.51 | 2.34 | 14 |
| 39.54 | 2.28 | 21 | 39.67 | 2.27 | 6 | 39.48 | 2.28 | 13 |

MODIFICATIONS OF THE TROMETAMOL SALT OF R-THIOCTIC ACID AS WELL AS A PROCESS FOR THEIR PRODUCTION

CROSS-REFERENCE TO RELATED APPLICATION

This application is a divisional of application Ser. No. 10/207,201, filed Jul. 30, 2002, now U.S. Pat. No. 6,844,449.

The present invention relates to new modifications of the trometamol salt of R-thioctic acid of the formula I,

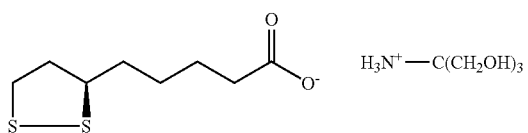

processes for their production, pharmaceutical preparations containing these modifications, and their medical application.

This compound is effective for example as an anti-inflammatory and cytoprotective agent (EP 427247) and is used to treat diabetes mellitus and insulin resistance (DE 4.343.593) as well as in glucose metabolic disorders of the central nervous system (DE 4.343.592) and as an appetite suppressant (DE 19.818.563), and may therefore be employed in pharmaceutical preparations (EP 702953).

The requirements that an active constituent must meet as regards the relevant physicochemical properties for galenical processibility and bioavailability are determined both by the nature and also by the production technology of the respective pharmaceutical preparation.

Particularly in the case of high dosage active constituents, among which is included the trometamol salt of R-thioctic acid, the physicochemical properties significantly influence the galenical processibility and bioavailability.

It is therefore advantageous with such an active constituent to have available, for various pharmaceutical preparations and production technologies, various modifications and mixtures thereof that exhibit different physicochemical properties.

Modifications of the compound I have not been known up to now.

The object of the present invention is accordingly to provide the compound I in various modifications as well as mixtures thereof, corresponding to the pharmaceutical requirements.

The two modifications, termed A and B, have different physicochemical properties. The in each case characteristic X-ray powder diffraction patterns are used to identify these two modifications of the compound of the formula I. The modifications differ furthermore in their DSC (differential scanning calorimetry) curves, by the in each case typical crystal forms, the different solubilities and/or dissolution rates, as well as by the different flow properties.

The X-ray diffraction patterns shown in FIGS. 1–6 were recorded with a powder diffractometer using CuK$_\alpha$ radiation.

The modification A is characterised by:
The X-ray diffraction pattern (see FIGS. 1–3 and FIG. 6), in which connection there are observed reflections inter alia at
14.87°2θ(5.96 Å), 19.99°2θ(4.44 Å), 20.88°2θ(4.25 Å), 22.78°2θ(3.90 Å), 24.53°2θ(3.63 Å), 25.66°2θ (3.47 Å), 30.05°2θ(2.97 Å) and at 37.29°2θ(2.41 Å) that do not coincide with the reflections of the other modification.

The melting point in the range from about 117.1° to 118.4° C.

The modification A occurs predominantly in the form of small platelets.

The modification B is characterised by:
The X-ray diffraction pattern (see FIGS. 1, 2 and 4 as well as FIG. 6), in which connection there are observed reflections inter alia at
13.80°2θ(6.41 Å), 15.22°2θ(5.82 Å), 17.50°2θ(5.06 Å), and at 23.48°2θ(3.79 Å)
that do not coincide with the reflections of the other modification.

The melting point in the range from about 115.2° to 116.8° C.

The modification B occurs predominantly in the form of aggregates.

The X-ray diffraction patterns of the modification mixtures A/B are characterised by overlapping of the reflections from A and B (mixture A/B=ca. 1:1, see FIGS. 1, 2 and 5, 6).

The solubility and/or dissolution rate of the modification A in water and organic solvents, such as for example lower alcohols, octanol and acetone, as well as their mixtures with water, is raised compared to modification B.

The angle of repose α of the modifications as a measure of the flowability and pourability is likewise different:

|  | Angle of Repose α[1] |
| --- | --- |
| Modification A | 46° |
| Modification B | 32° |
| Modification mixture A/B = 1:1 | 34° |

[1] Determined according to R. Voigt, Lehrbuch der pharmazeutischen Technologie, 3$^{rd}$ Edition 1979, p. 165

It is generally known that R-thioctic acid readily polymerises and has a tendency to undergo such reactions, particularly in polar media.

It is therefore surprising that in the reaction of R-thioctic acid with trometamol, polymer-free products may be obtained if the trometamol is metered into the solution of R-thioctic acid in polar solvents, such as for example lower alcohols, optionally under the addition of water, and the suspension obtained is warmed in order to effect dissolution.

The term "lower alcohols" is understood in this connection to denote straight-chain or branched alcohols with 1 to 6 C. atoms.

The crystallisation then takes place under cooling. Further product is obtained from the mother liquor by concentrating the solution by evaporation under gentle conditions and cooling.

Surprisingly the modifications A and B of the compound I as well as their mixtures of arbitrary composition can be produced by salt formation of R-thioctic acid with trometamol in suitable polar solvents such as for example lower alcohols, as well as by modification transformation under special reaction conditions.

Accordingly, either pure modifications of the compound I or alternatively mixtures thereof of varying composition may be prepared for the production of various pharmaceutical preparations.

The preparation of the modifications A and B and their mixtures by salt formation of R-thioctic acid with trometamol depends on the purity of the R-thioctic acid that is used (content of trace impurities resulting from the synthesis).

Thus, the modification A is obtained with R-thioctic acid that has been obtained by racemate resolution according to DE 4.137.773 (hereinafter denoted as synthesis pathway a). On the other hand with R-thioctic acid in the preparation of which sulfur is introduced at the end of the synthesis (hereinafter denoted as synthesis pathway b; for example DE 4.037.440, DE 19.533.881, DE 19.533.882, DE 19.709.069), the modification B is obtained as main product, together with a minor amount of A. By means of one or more additional purification steps carried out on the R-thioctic acid obtained by synthesis pathway b (e.g. recrystallisation from inert solvents such as cyclohexane, cyclohexane/ethyl acetate (in particular 19:1), n-heptane/toluene, n-hexane/toluene, optionally under the addition of water and/or dilute mineral acid as well as dissolution and crystallisation from dilute alkali solution/dilute mineral acid under simultaneous extraction, for example with cyclohexane/ethyl acetate, trace impurities resulting from the synthesis can be successively removed so that in the salt formation either a modification A/B or the modification A are formed as main products. On the other hand by adding nucleophilic compounds, such as for example sodium sulfite or 6,8-dimercaptooctanoic acid, in the salt formation with R-thioctic acid prepared by the synthesis pathway a the modification B is obtained as the main product.

The modifications may also be prepared by modification transformation, in which a complete or partial transformation of A after B as well as of B after A may take place.

In this connection it is possible to use the pure modifications A and B as well as their mixtures. When using mixtures the transformation preferably proceeds in the direction of the formation of a pure modification.

The following methods may be employed:
Recrystallisation from lower alcohols, optionally under the addition of water
Prolonged heating in lower alcohols, optionally under the addition of water, at temperatures up to the boiling point, followed by cooling crystallisation
Concentration by evaporation of solutions in lower alcohols, optionally under the addition of water, by distilling off the solvent under normal pressure or in vacuo.
Reprecipitation from solvent mixtures.
Conversion of the salt I suspended in solvents.
Thermal phase conversion below the melting point or by melting.

Preparation of Modification A
Recrystallisation of modification B or A/B mixtures from lower alcohols.
Distilling off the solvent in vacuo from solutions of the modification B or A/B mixtures in lower alcohols.
Suspension of modification B or of A/B mixtures in lower alcohols, optionally under the addition of water, at temperatures of about 0° to 60° C., preferably at about 20° to 40° C., and stirring times of in general 1 to 24 hours, in particular about 2 to 15 hours.
Reprecipitation by addition of hydrocarbons to the solution of the modification A in lower alcohols.

Preparation of Modification B
Recrystallisation of modification A or A/B mixtures from lower alcohols, optionally under the addition of water.
Distilling off the solvent from solutions of the modification A in lower alcohols.
Heating a melt of the modification A preferably for about 10 to 40 minutes at ca. 115°–130° C., in particular for 15 to 25 minutes at about 115°–120° C., and crystallisation by cooling.
Recrystallisation of modification A from lower alcohols, optionally under the addition of water, with the addition of nucleophilic compounds such as for example sodium sulfite or 6,8-dimercaptooctanoic acid.

Preparation of Mixtures of Modifications A/B
Heating a solution of the modification A in lower alcohols at the reflux temperature generally for ca. 2 to 12 hours, preferably for about 4 to 8 hours, followed by cooling crystallisation.
Distilling off the solvent from solutions of the modification A in lower alcohols, optionally under the addition of water.
Brief melting of the modification A and crystallisation under cooling.
Reprecipitation by addition of acetone to the solution of the modification A in water or dimethylformamide.
Recrystallisation of modification A from lower alcohols, optionally under the addition of water, as well as addition of nucleophilic compounds such as for example sodium sulfite or 6,8-dimercaptooctanoic acid.
Recrystallisation of modification A from dipolar-aprotic solvents such as for example N,N-dimethylacetamide, ethylene glycol dimethyl ether, 1,2-dichloroethane, methyl ethyl ketone, and dimethyl carbonate.
Recrystallisation of modification A or B from lower alcohols, optionally under the addition of water.

The modifications A and B as well as their mixtures may be processed in a conventional way with suitable carriers and/or auxiliary substances into pharmaceutical preparations. Preferred application forms are tablets and capsules.

The modifications are for example valuable agents for treating insulin resistance, diabetes mellitus, and glucose metabolic disturbances of the central nervous system. The production processes for the modifications A and B as well as their mixtures will be described in more detail hereinafter with the aid of examples.

EXAMPLES

The modifications of the compound I were, after suction filtration, washed with the relevant cooled solvent and dried for 2 hours at 50° C. unless otherwise stated.

Formation of Modifications in the Preparation of the Trometamol Salt of R-Thioctic Acid Example 1

12.1 g (0.1 mole) of trometamol were added to a solution of 41.2 g (0.2 mole) of R-thioctic acid (produced according to process a) in 220 ml of ethanol (96%) and heated while stirring to 55° C.

1 g of Diacel (filter aid) was added to the solution, heated for 20 minutes at 55°–57° C., suction filtered until clear, slowly cooled and stirred at −5° C. to −10° C. for 2 hours.

Yield: 58.0 g (88.6% of theory) of I, modification A.

A further 1.7 g (2.6% of theory) of I, modification A, were obtained by concentrating by evaporation the mother liquor to ca. ⅕ of its original volume.

Example 2

41.2 g (0.2 mole) of R-thioctic acid (produced according to process a) were dissolved in 600 ml of ethanol (anhydrous). 24.2 g (0.2 mole) of trometamol were added while stirring, and the mixture was heated to 50°–55° C. to dissolve the trometamol and after addition of 2 g of Diacel was stirred for ca. 10 minutes at 50°–55° C. and suction filtered until clear. The solution was then slowly cooled (over 3–4 hours) at a roughly uniform cooling rate to −5° C. and stirred for a further 4-5 hours at −5° to −10° C.

Yield: 55.5 g (84.9% of theory) of I, modification A.

A further 4.1 g (6.3% of theory) of I, modification A, were obtained by concentrating by evaporation the mother liquor to ca. 20%.

Example 3

41.2 g (0.2 mole) of R-thioctic acid (produced according to process a) were dissolved in 230 ml of ethanol (anhydrous). 24.2 g (0.2 mole) of trometamol were added and the mixture was stirred at 55°–60° C. until all the trometamol had dissolved. After suction filtration the resultant clear solution was slowly cooled to 0° to 5° C., stirred for 2 to 4 hours in this temperature range, suction filtered, washed with cold ethanol and dried.

Yield: 61.0 g (93.1% of theory) of I, modification A.

A further 2.4 g (3.7% of theory) of I, modification A, were obtained by concentrating by evaporation the mother liquor in vacuo to ca. 20%.

Example 4

41.2 g (0.2 mole) of R-thioctic acid (produced according to process b followed by recrystallisation from cyclohexane/ethyl acetate/water corresponding to Example 31) were dissolved in 600 ml of ethanol (anhydrous). 24.2 g (0.2 mole) of trometamol were then added and the solution was heated to 50°-55° C. while stirring. 2 g of Diacel were added to the solution, which was stirred for 20 minutes, suction filtered until clear, and slowly cooled. The solution was seeded at 30° C., and stirred for 4 hours in the range from −5° to −10° C.

Yield: 56.1 g (85.7% of theory) of I, modification A.

A further 6.7 g (10.2% of theory) of I, modification A, were obtained by concentrating by evaporation the mother liquor to ca. ⅕ of the original volume.

Example 5

54.9 g (83.9% of theory) of I, modification mixture A/B (ca. 1:1) were obtained, similarly to Example 4, as a first crystallisate from R-thioctic acid (produced according to process b followed by recrystallisation once from cyclohexane). 6.8 g (10.4% of theory) of I, modification A, were then obtained by concentration by evaporation of the mother liquor.

Example 6

25.8 g (0.125 mole) of R-thioctic acid (produced according to process b) were dissolved in 375 ml of ethanol (anhydrous). 15.13 g (0.125 mole) of trometamol were then added and the mixture was heated at 50°–55° C. while stirring until the trometamol had dissolved. After addition of 1.25 g of Diacel and suction filtration of the solution until clear, the latter was slowly cooled, seeded at 30° C., and cooled for a further 4 hours at −5° to −12° C.

Yield: 28.1 g (68.6% of theory) of I, modification B.

9.3 g (22.6% of theory) of I, modification A, were obtained by concentration by evaporation of the mother liquor to 70 ml and cooling.

Example 7

41.2 g (0.2 mole) of R-thioctic acid (produced according to process b) were dissolved in 250 ml of ethanol (anhydrous). 24.2 g (0.2 mole) of trometamol were then added and the solution was heated at 55°–57° C. while stirring until the trometamol had dissolved.

After addition of 1.25 g of Diacel and suction filtration of the solution until clear, the latter was slowly cooled (ca. 1–2 hours) and stirred at −5° to −10° C. for 2 hours.

Yield: 55.0 g (84.1% of theory) of I, modification B.

5.7 g (8.7% of theory) of I, modification A, were obtained by concentration by evaporation of the mother liquor to 70 ml and cooling.

Example 8

41.2 g (0.2 mole) of R-thioctic acid (produced according to process b) were dissolved in 220 ml of ethanol (anhydrous). 24.2 g (0.2 mole) of trometamol were then added and the solution was heated to 57° C.

2 g of Diacel were added to the solution, which became clear after 10 minutes, and the latter was stirred for 20 minutes at 55°–57° C., suction filtered until clear, and slowly cooled. The solution was stirred for 2 hours at −5° to −10° C.

Yield: 57.8 g (88.4% of theory) of I, modification B.

3.7 g (5.7% of theory) of I, modification A, were obtained by concentration by evaporation of the mother liquor to ca. 20% followed by cooling.

Example 9

20.6 g (0.1 mole) of R-thioctic acid (produced according to process a) were dissolved in 300 ml of ethanol (anhydrous). Following the addition of 12.1 g (0.1 mole) of trometamol and 0.5 g of 6,8-dimercaptooctanoic acid the mixture was heated at 55° C. until the trometamol had dissolved. After addition of 1 g of Diacel the solution was stirred for 20 minutes at 53°–55° C., suction filtered until clear, and then slowly cooled. The solution was then stirred for 2 hours at −8° to −12° C.

1.9 g (5.8% of theory) were recovered from the flask wall (modification mixture B>A).

20.2 g (61.8% of theory) of I, modification B, were obtained by concentrating by evaporation the mother liquor to half the original volume and cooling overnight at −5° to −10° C.

1.9 g (5.8% of theory) of I, modification A, were obtained by further concentration by evaporation to ca. half the original volume followed by cooling.

Example 10

20.6 g (0.1 mole) of R-thioctic acid (produced according to process a) were dissolved in 110 ml of ethanol (96%). 12.1 g (0.1 mole) of trometamol as well as 2 g of sodium sulfite were then added and the whole was heated to 55° C. After addition of 1 g of Diacel the solution was stirred for 20 minutes at 53°–55° C., suction filtered until clear, and slowly cooled. The solution was then stirred for 2 hours at −5° to −10° C.

8.1 g (yield 24.8% of theory) of I, modification A, were obtained.

The mother liquor was concentrated by evaporation to about half the original volume and cooled overnight at −5° to −10° C.

19.1 g (yield 58.4% of theory) of I, modification B, were obtained.

Production of Modifications by Transformation

Example 11

10 g of I, modification B, were dissolved in 85 ml of ethanol (anhydrous) at 50°–55° C. The solution was slowly cooled to −5° to −10° C. while stirring, and was then seeded with I, modification A, at 30° C.

After stirring (2 hours) at −5° to −10° C. and standing overnight in a deep-freeze cabinet, 5.4 g (54% of theory) of I, modification B, were recovered.

4.0 g (40% of theory) of I, modification A, were obtained by concentration by evaporation of the mother liquor to ⅕ of the original volume and cooling in a deep-freeze cabinet overnight.

Example 12

1 g of I, modification B, was dissolved in 10 ml of ethanol (anhydrous) at 55° C., the solvent was evaporated at room temperature, and the residue was investigated after drying (2 hours, 50° C.): I, modification A.

Example 13

30 ml of n-heptane are added at 57° C. to a solution of 3 g of I, modification B, in 25 ml of anhydrous ethanol and then cooled to −5° to −10° C.

The crystallisate is dried (2 hours, 50° C.).

Yield: 2.5 g (75% of theory) of I, modification A.

Example 14

2 g of a mixture consisting of 80% of modification A and 20% of modification B were suspended in 3 ml of ethanol (96%) and stirred for 11 hours at 35° C., the pure modification A thereby being obtained.

Example 15

20 g of I, consisting of ca. 50% of each of the modifications A and B, were dissolved in 170 ml of ethanol (anhydrous) at 50°–55° C., and after addition of 0.5 g of Diacel the solution was suction filtered until clear. The filtrate was rapidly cooled to −5° to −10° C. while stirring, and stirred for a further 2 hours at this temperature.

Yield: 16.8 g (84% of theory) of I, modification A.

Example 16

20 g of I, modification A, were dissolved in 170 ml of ethanol (anhydrous) at 50°–55° C. The filtrate was slowly cooled to −5° to −10° C., and was then seeded at 31° C. The mixture was stirred for 2 hours at −5° to −10° C.

16.9 g (84.5% of theory) of I, modification A, were recovered.

2.0 g (10% of theory) of I, modification B with traces of A, were obtained by concentration by evaporation of the mother liquor to ⅕ of the original volume followed by cooling.

The same result was also obtained without seeding.

Example 17

40 g of I, mixture A>B, were dissolved at 50°–55° C. in 120 ml of ethanol (96%), rapidly cooled to −5° to −10° C., and stirred for 2 hours in the same temperature range.

Yield: 34 g (85% of theory) of I, modification B.

Example 18

10 g of I, modification A, were heated for 6 hours under reflux in 85 ml of ethanol (anhydrous), and the solution was then cooled and stirred for one hour at −5° to −10° C.

Yield: 8.3 g (83% of theory) of I, mixture of the modifications A and B (ca. 1:1).

The mother liquor was concentrated to 20% by evaporation: 0.91 g (9.1% of theory) of I, modification B.

Example 19

8.6 g of I (yield 86% of theory) in the form of a modification mixture (B>A) were obtained as first crystallisate by heating under reflux (6 hours) 10 g of I, modification A, in 30 ml of ethanol (96%), followed by cooling and stirring (1 hour at −5° to −10° C.).

Example 20

15 g of I, modification B, were dissolved in 70 ml of ethanol (96%) at 55° C. The solution was cooled and stirred for 2 hours at −5° to −8° C.

Yield: 12.8 g (84.8% of theory) of I, modification mixture A/B (ca. 1:1).

0.6 g (3.9% of theory) of I, modification A, was obtained by concentration by evaporation of the mother liquor to ca. 20% followed by cooling.

Example 21

5 g of I, modification A, were dissolved at 50°–55° C. in 200 ml of isopropanol. The solution was rapidly cooled and then stirred for 1 hour at −5° to −10° C.

4.2 g (84% of theory) of I, modification mixture A/B, were obtained.

A further 0.4 g (8% of theory) of I, modification mixture A/B, was obtained by concentration by evaporation of the mother liquor to 20% followed by cooling.

Example 22

3 g of I, modification A, were dissolved in 3 ml of N,N-dimethylacetamide at 50°–55° C. The solution was cooled and stirred at −5° to −10° C. for 1 hour.

Yield: 1.6 g (53.3% of theory) of I, modification mixture (A>B).

Example 23

10 g of I, modification A, were dissolved at 55° C. in 90 ml of ethanol (anhydrous). The majority of the solvent was distilled off under normal pressure, and the remainder under a vacuum. The oil obtained crystallised on cooling: I, modification B, quantitative yield.

Example 24

10 g of I, modification A, were dissolved at 55° C. in 30 ml of ethanol (96%). The solution was then concentrated by evaporation on a rotary evaporator up to a maximum bath temperature of 100° C., and was finally evaporated in vacuo. The oil crystallised on cooling: mixture (ca. 1:1) of the modifications A and B, quantitative yield.

Example 25

2 g of I, modification A, were melted at a bath temperature of 115°–120° C. and maintained for 20 minutes at this temperature. The crystallisate obtained on cooling consisted mainly of modification B with traces of A in addition to polymer.

Example 26

2 g of I, modification A, were briefly melted at a bath temperature of ca. 140° C. and then rapidly cooled. The crystallisate consisted of an A/B modification mixture together with polymer.

Example 27

400 ml of acetone were added to a solution of 3 g of I, modification A, in 8 ml of water and the whole was cooled at −5° to −8° C. (2 hours)
Yield: 1.8 g (60% of theory) of I, modification mixture (B>A).

Example 28

80 ml of acetone were added to a solution of 3 g of I, modification A, in 12 ml of dimethylformamide. The solution was cooled to −5° and stirred for 90 minutes at this temperature.
Yield: 2.75 g (91.3% of theory) of I, modification B together with traces of A.

Example 29

20 g of I, modification A, and 2 g of sodium sulfite were dissolved or suspended at 50°–55° C. in 50 ml of ethanol (96%). After the addition of 1 g of Diacel the solution was suction filtered until clear, slowly cooled to −6° to −8° C. and stirred for 2 hours at this temperature.

Yield: 15.9 g (79.5% of theory) of I, modification mixture (B>A).

Example 30

10 g of I, modification A, and 0.25 g of 6,8-dimercapto-octanoic acid were dissolved at 50°–55° C. in 85 ml of ethanol (anhydrous). After the addition of 1 g of Diacel the solution was suction filtered until clear, slowly cooled to −8° to −12° C., and stirred for 2 hours in this temperature range.
Yield: 1.9 g (19% of theory) of I, modification mixture (B>A).
6.1 g (61% of theory) of modification B were obtained by concentration by evaporation of the mother liquor to ca. 50% followed by cooling.

Example 31

100 g of R-thioctic acid (produced according to process b) were dissolved in a mixture consisting of 760 ml of cyclohexane and 40 ml of water-saturated ethyl acetate (water content: 3.2%) at 40°–42° C. After addition of 5 g of Diacel the solution was suction filtered until clear, slowly cooled to −5°, stirred for 1 hour at this temperature, suction filtered, washed with cyclohexane and dried at 30° C.
Yield: 87.5 g (87.5% of theory) of pure R-thioctic acid.

The invention claimed is:
1. Modification A of the compound I

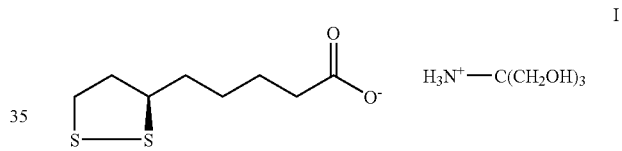

characterised by the X-ray diffraction pattern in which reflections not coinciding with the reflections of the other modifications are observed inter alia at 14.87°2θ20(5.96 Å), 19.99°2θ(4.44 Å), 20.88°2θ(4.25 Å), 22.78°2θ(3.90 Å), 24.53°2θ(3.63 Å), 25.66°2θ(3.47 Å), 30.05°2θ(2.97 Å) and at 37.29°2θ(2.41 Å).

2. Modification B of the compound I characterised by the X-ray diffraction pattern in which reflections not coinciding with the reflections of the other modification are observed inter alia at 13.80°2θ(6.41 Å), 15.22°2θ(5.82 Å), 17.50°2θ6 (5.06 Å) and at 23.48°2θ(3.79 Å).

* * * * *